United States Patent [19]

Martin et al.

[11] 4,394,517

[45] Jul. 19, 1983

[54] QUATERNARY AMMONIUM FUNCTIONAL SILICON COMPOUNDS

[75] Inventors: Eugene R. Martin, Onsted, Mich.; Jeffrey A. Tripp, Hillsdale, Australia

[73] Assignee: SWS Silicones Corporation, Adrian, Mich.

[21] Appl. No.: 380,487

[22] Filed: May 21, 1982

[51] Int. Cl.³ .............................................. C07F 7/10
[52] U.S. Cl. ................................. 556/419; 556/418; 8/115.5
[58] Field of Search ............................... 556/419, 418

[56] References Cited

U.S. PATENT DOCUMENTS

| | | | |
|---|---|---|---|
| 2,415,017 | 1/1947 | MacKenzie | 556/419 X |
| 2,637,623 | 5/1953 | Janes | 556/419 X |
| 2,838,423 | 6/1958 | Gilkey | 556/419 X |
| 3,700,844 | 10/1972 | Domba | 556/419 X |
| 3,734,763 | 5/1973 | Plueddemann | 556/419 X |
| 3,819,675 | 6/1974 | Plueddemann | 556/418 X |
| 4,312,993 | 1/1982 | Martin | 556/419 |
| 4,342,742 | 8/1982 | Sebag et al. | 556/418 X |

*Primary Examiner*—Paul F. Shaver

[57] ABSTRACT

Quaternary ammonium functional silicon compounds are prepared by reacting carboxylic acid functional quaternary ammonium compounds with aminofunctional silicon compounds. These quaternary ammonium functional silicon compounds are antistatic finishes for textiles.

18 Claims, No Drawings

QUATERNARY AMMONIUM FUNCTIONAL SILICON COMPOUNDS

The present invention relates to quaternary ammonium compounds and more particularly to quaternary ammonium functional silicon compounds and their use as antistatic agents for textile materials.

BACKGROUND OF THE INVENTION

Quaternary ammonium silicon compounds have been described, for example, in U.S. Pat. No. 3,471,541 to Morehouse, in which a tertiary amine is prepared by reacting an alkenyl ether of a tertiary hydroxy polyalkyleneoxy alkylamine with a hydrosilicon compound (i.e., a silane or siloxane containing silicon-bonded hydrogen) in the presence of a platinum catalyst. The resultant tertiary amines are then reacted with hydrocarbyl halides, monocarbylic acids and the hydrocarbyl esters of haloalkanoic acids to form the corresponding quaternary ammonium silicon compounds.

U.S. Pat. No. 3,661,963 to Pepe et al describes quaternary ammonium salts of chloromethylated silanes or siloxanes which are useful as antistatic agents. These quaternary ammonium salts are prepared by reacting a tertiary amine of the formula $R_3N$, where R is a monovalent organic radical, with a chloromethylarylsilane or chloromethylaralkylsilane.

U.S. Pat. No. 3,734,763 to Plueddemann describes cationic unsaturated amine functional silane coupling agents which can be applied to glass fibers to minimize the build-up of static charge on the fibers. These amine functional silane coupling agents can be prepared by reacting conjugated unsaturated alkyl halides with an aminofunctional silane.

In contrast to the quaternary ammonium silicon compounds described above, the quaternary ammonium functional silicon compounds of the present invention impart antistatic properties to textile materials which withstand repeated washings. Moreover, the quaternary ammonium functional silicon compounds, especially the quaternary ammonium functional organopolysiloxanes are prepared from commercially available materials.

Therefore, it is an object of this invention to provide a process for preparing novel quaternary ammonium functional silicon compounds. Another object of this invention is to provide quaternary ammonium functional silicon compounds which impart antistatic properties to textile materials. Still another object of this invention is to provide quaternary ammonium functional silicon compounds which adhere to textile materials after repeated washings. A further object of the present invention is to provide a process for preparing quaternary ammonium functional organopolysiloxanes which impart antistatic properties to textile materials.

SUMMARY OF THE INVENTION

The foregoing objects and others which will become apparent from the following description are accomplished in accordance with this invention, generally speaking, by providing a process for preparing quaternary ammonium functional silicon compounds which comprises reacting carboxylic acid functional quaternary ammonium compounds with aminofunctional silicon compounds. These compositions may be applied to textile fibers to provide antistatic properties.

DETAILED DESCRIPTION OF THE INVENTION

The carboxylic acid functional quaternary ammonium compounds which are reacted with the aminofunctional silicon compounds may be represented by the formulas

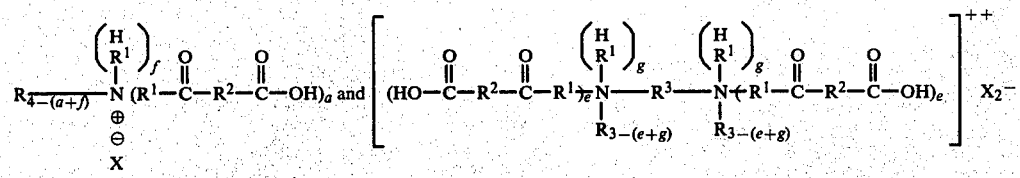
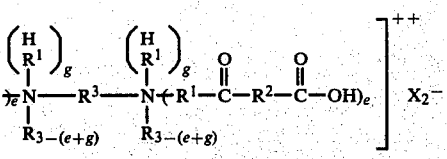

wherein R which may be the same or different is a monovalent hydrocarbon radical having from 1 to 22 carbon atoms, $R^1$ is a hydrocarbonoxy radical represented by the formula

in which the terminal carbon atom is linked to the nitrogen atom, $R^2$ which may be the same or different is a divalent hydrocarbon radical selected from the group consisting of $(CH_2)_y$, $CH=CH$, a cyclic divalent hydrocarbon radical selected from the group consisting of $C_6H_4$, $C_6H_8$, $C_6H_{10}$ and $C_{10}H_6$, $R^3$ is a divalent hydrocarbon radical having from 2 to 10 carbon atoms, X is an anionic radical, a is a number of from 1 to 4, e is a number of from 1 to 3, f is a number of from 0 to 3, g is a number of from 0 to 2, in which the sum of $a+f$ cannot exceed 4, the sum of $e+g$ cannot exceed 3, n is 2, 3 or 4, r is a number of from 1 to 50, and y is a number of from 0 to 10.

The carboxylic acid functional quaternary ammonium compounds may be prepared by reacting carbinol functional quaternary ammonium compounds of the formulas

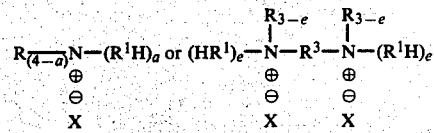

wherein R, $R^1$, $R^3$, X, a and e are the same as above with dicarboxylic acids or cyclic anhydrides thereof to form the carboxylic acid functional quaternary ammonium compounds.

The resultant carboxylic acid functional quaternary ammonium compounds are then reacted with aminofunctional compounds selected from the group consisting of:

(a) Silanes having the formula

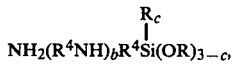

(b) Siloxanes having at least one unit of the formula

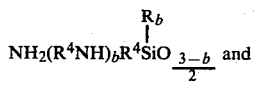

(c) mixtures thereof,
R is the same as above, $R^4$ which may be the same or different is a radical selected from the group consisting of a saturated divalent hydrocarbon radical having up to 10 carbon atoms, a divalent hydrocarbonoxy radical in which the oxygen is in the form of an ether linkage and an unsaturated divalent hydrocarbon radical having from 3 to 10 carbon atoms, b is 0, 1 or 2, and c is 0, 1, 2 or 3.

The siloxanes (b) may also contain units of the formula

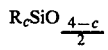

where R and c are the same as above.

The siloxanes may also be endblocked with silanol, alkoxy, aryloxy or triorganosiloxy groups.

The carboxylic acid functional quaternary ammonium compounds are reacted with the aminofunctional silicon compounds at a temperature of from about 0° C. up to about 175° C. and more preferably from about 25° C. to about 140° C. It is preferred, although it is not essential, that the reaction be conducted in the presence of a non-protic solvent. Suitable examples of non-protic solvents are aliphatic hydrocarbon solvents such as hexane and heptane; aromatic hydrocarbon solvents such as benzene, toluene and xylene; ethers such as diglyme and diethyl ether; chlorinated hydrocarbon solvents, such as 1,1,1 trichloroethane, perchloroethane and carbon tetrachloride.

Although the reaction time may vary over a broad range, it is preferred that the reaction time be limited at temperatures above about 100° C. in order to avoid degradation of the quaternary ammonium compound.

The mole ratio of the carboxylic acid group linked to the quaternary ammonium compound to amine group linked to the silicon compound may vary over a wide range, e.g., from about 4:1 to 1:3, with the proviso that at least one carboxylic acid group is reacted with one amine group.

After the completion of the reaction the solvent may be removed at a temperature of from about 25° to 150° C., preferably at reduced pressure.

The reaction between the carboxylic acid functional quaternary ammonium compound and the aminofunctional silicon compound forms an ammonium carboxylate. The ammonium carboxylate may be heated to an elevated temperature to remove a mole of water per ammonium carboxylate to form the corresponding amide.

The water may be removed by using a non-protic solvent, e.g., toluene, which azeotropes with the water, or the water can be removed in vacuum. However, if the ammonium carboxylate is desired then the removal of the water and the formation of the amide must be avoided.

The carboxylic acid functional quaternary ammonium compounds employed in this invention may be prepared by reacting dicarboxylic acids or cyclic anhydrides thereof with the carbinol functional quaternary ammonium compounds at a temperature of from 50° to 175° C. and more preferably at a temperature of from 75° to 150° C. Generally, it is preferred that the reaction be conducted in the presence of non-protic solvents.

The non-protic solvents described above may be used in preparing the carboxylic acid functional quaternary ammonium compounds. The solvent may be removed in vacuum at 25° to 150° C.

The mole ratio of cyclic anhydride to carbinol group may vary over a wide range. For example, the mole ratio of cyclic anhydride to carbinol group may range form 1:1 to 1:4 with the proviso that at least one carbinol group is reacted with the cyclic anhydride molecule.

When dicarboxylic acids are reacted with the carbinol functional quaternary ammonium compounds, then it is preferred that the reaction be conducted in the presence of a non-protic solvent which is capable of azeotroping with the water byproduct. The solvent may then be removed in vacuum at 25° to 150° C. When the reaction is conducted in the absence of a non-protic solvent, the water may be removed in vacuum.

A catalyst may be employed to accelerate the reaction between the dicarboxylic acid and the carbinol functional quaternary ammonium compounds. Examples of suitable catalysts are bases, such as alkali metal hydroxides or alkoxides; acids such as hydrochloric acid; titanates such as titanium tetrachloride and tin compounds such as dibutyl tin dilaurate. Generally, a catalyst level of from about 0.1 percent to 10 percent, based on the weight of the reactants will accelerate the reaction.

The mole ratio of carboxylic acid group to carbinol group may vary over a wide range. For example, the mole ratio of carboxylic acid group to carbinol group may range from 8:1 to 2:1, with the proviso that at least one carboxylic acid group be reacted with one carbinol group.

Suitable examples of dicarboxylic acids which may be employed to form the carboxylic acid functional quaternary ammonium compounds are oxalic acid, malonic acid, succinic acid, glutaric acid, phthalic acid, adipic acid, pimelic acid, suberic acid, azelaic acid and sebacic acid. Suitable examples of cyclic anhydrides are succinic anhydride, glutaconic anhydride, maleic anhydride, 1,2 cyclohexane dicarboxylic anhydride, 1-cyclohexene-1,2-dicarboxylic anhydride, 3-cyclohexene-1,2-dicarboxylic anhydride, 4-cyclohexene-1,2 dicarboxylic anhydride, 1,8-naphthalic acid anhydride and phthalic anhydride.

The carbinol functional quaternary ammonium compounds may be prepared by conventional processes known in the art. For example, they may be prepared by reacting an alkyl halide which also contains an alcohol group with an amine or ammonia.

The counter-ion in the carbinol functional quaternary ammonium compound can be any anionic group. Suitable examples of anionic groups are halogen, methyl sulfate and phosphate anions.

Suitable examples of monovalent hydrocarbon radicals represented by R are alkyl radicals, such as methyl, ethyl, propyl, butyl, hexyl, octyl, decyl, dodecyl, hexadecyl, octadecyl radicals; alkenyl radicals such as the vinyl, allyl as well as octadecenyl radicals; aryl radicals such as phenyl and naphthyl radicals; alkaryl radicals such as, tolyl, xylyl and ethylphenyl radicals; cycloalkyl radicals such as cyclobutyl, cyclohexyl and cyclodecyl radicals; aralkyl radicals such as benzyl, 2-phenylethyl and 2-phenylpropyl radicals.

Examples of suitable divalent hydrocarbonoxy radicals represented by $R^1$ are radicals of the formula $$(C_nH_{2n}O)_r$$

where the terminal carbon atom is linked to the nitrogen atom, r is an average number of from 1 to 50, and n is 2, 3, or 4.

Examples of suitable divalent hydrocarbon radicals represented by $R^1$, and $R^2$ having up to 10 carbon atoms are methylene, ethylene, trimethylene, tetramethylene, pentamethylene, hexamethylene, octamethylene and decamethylene radicals. Examples of divalent aryl radicals are phenylene, cyclohexenylene and naphthenylene. Examples of suitable divalent hydrocarbon radicals represented by $R^3$ are ethylene, trimethylene, tetramethylene, pentamethylene, hexamethylene, octamethylene and decamethylene radicals.

Examples of suitable divalent radicals represented by $R^4$ are hydrocarbon radicals such as ethylene, trimethylene, hexamethylene, and octamethylene radicals and hydrocarbonoxy containing radicals of the formula $$(C_2H_4O)_r(CH_2)_z, (C_3H_6O)_r(CH_2)_z \text{ and } (C_4H_8O)_r(CH_2)_z$$

where r is from 1 to 50 and z is a number of from 1 to 10.

Suitable examples of unsaturated divalent radicals represented by $R^4$ are propenylene, isopropenylene, 2-butenylene, isobutenylene, sec-butenylene, 2-pentenylene, 3-pentenylene, hexenylene, octenylene and decenylene.

Suitable examples of aminofunctional silanes which may be used in preparing the compositions of this invention are beta-aminopropyltriethoxysilane, gamma-aminopropyltrimethoxysilane, methyl-beta-(aminoethyl)-gamma-aminopropyldimethoxysilane, omega-aminohexyltributoxysilane, beta-(aminoethoxy)propyltrimethoxysilane, beta-(aminoethoxy)hexyltriethoxysilane, beta-(aminopropoxy)butyltributoxysilane. Other aminofunctional silanes which may be used are those having the formulas

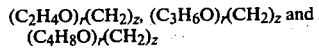

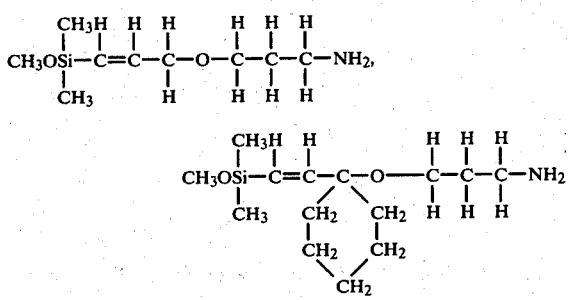

The aminofunctional siloxanes employed in the process of this invention are well known in the art. They may be prepared in accordance with the process described in U.S. Pat. No. 2,947,771 to Bailey, in which an aminofunctional silane is equilibrated with a siloxane in the presence of an alkali-metal hydroxide. Also, they may be prepared in accordance with the process described in U.S. Pat No. 3,598,853 to Friedman et al, in which an aminofunctional silane is condensed with a silanol terminated polydiorganosiloxane. Other methods for preparing aminofunctional siloxane fluids are described in U.S. Pat. Nos. 3,890,269 to Martin; 2,930,809 to Jex et al and 3,045,036 to Jex et al. The aminofunctional siloxanes described in these references and their methods of preparation are incorporated herein by reference.

These quaternary ammonium functional silicon compounds may be mixed with various diluents. Examples of suitable diluents are organic solvents such as alcohols, e.g., ethanol and 1-propanol; aliphatic solvents such as heptane and iso-octane; aromatic solvents such as toluene and xylene and chlorinated solvents such as chloroform and 1,1,1-trichloroethane. Other diluents are water and organosiloxanes having a viscosity up to 100,000 mPa.s at 25° C., such as hexamethyldisiloxane, diorganopolysiloxanes such as dimethylpolysiloxanes, cyclic siloxanes, organofunctional polysiloxanes such as aminofunctional, mercaptofunctional and carboxylic acid functional polysiloxanes.

The quaternary ammonium functional silicon compounds of this invention may be used to treat textile materials to impart antistatic properties thereto.

These quaternary ammonium functional silicon compounds may be applied to textile fabrics in concentrated form or in the presence of a diluent. The amount of quaternary ammonium functional silicon compound present in the diluent may range from about 0.25 to 99 percent, preferably from about 2 to 50 percent by weight based on the weight of the quaternary ammonium functional silicon compound and the diluent.

The quaternary ammonium functional silicon compounds of this invention, and if desired other substances, may be applied to all textile materials, preferably organic textile materials on which polyorganosiloxanes have been or could have been applied heretofore. Examples of such textile materials are wool, cotton, rayon, hemp, natural silk, polypropylene, polyethylene, polyester, polyurethane, polyamide, cellulose acetate, polyacrylonitrile fibers, and mixtures of such fibers. The textile materials may consist of staple fibers or monofilaments.

The quaternary ammonium functional silicon compounds of this invention and other substances, if desired, may be applied to the textile materials by any means known in the art, such as by spraying, immersion, padding, calendering or by gliding the fibers across a base which has been saturated with the quaternary ammonium functional silicon compounds of this invention and other materials, if desired.

Generally, the solids add-on is in the range of from 0.001 to 20 percent and more preferably from about 0.05 to 10 percent, based on the original weight of the textile material.

After the textile material has been treated, it is dried at an elevated temperature, e.g., from about 50° to 200° C. for a brief period of time. e.g., from about 3 to 15 minutes.

Specific embodiments of this invention are further illustrated in the following examples in which all parts are by weight unless otherwise specified.

EXAMPLE 1

(a) Preparation of carboxylic acid functional quaternary ammonium compound.

To a flask containing 320 parts of a carbinol functional quaternary ammonium compound represented by the formula

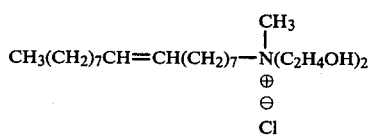

is added 158.8 parts of succinic anhydride and 925 parts of toluene and heated for 10 hours at 85° C. Infrared Analysis of the product shows the absence of succinic anhydride. The acid content of the solution is 1.1 milliequivalents/g. (Calculated 1.1 milliequivalents/g).

(b) Preparation of the aminofunctional silicon compound.

To a flask containing 221 parts of 3-aminopropyltriethoxysilane is added 2220 parts of octamethylcyclotetrasiloxane and 2.5 parts of a 25 percent by weight solution of tetramethylammonium hydroxide dissolved in methanol and heated at 80° C. for 2.5 hours. Then the temperature is increased to 140° C. and maintained for 1 hour. The resultant product is a 3-aminopropyl functional dimethylpolysiloxane endblocked with ethoxy groups and having a viscosity of 27 cs. at 25° C. The base equivalent is 0.42 milliequivalents/g. (Calculated 0.4 milliequivalents/g).

(c) Preparation of quaternary ammonium functional polydimethylsiloxane.

To a flask containing 152.8 parts of the toluene solution containing the carboxylic acid functional quaternary ammonium compound prepared in Example 1(a) above is added 400 parts of the 3-aminopropyl functional dimethylpolysiloxane prepared in Example 1(b) above. After a slight exotherm, the reactants are heated at 65° C. for three hours and then filtered. The chloride content of the resultant product is 5,000 ppm (parts per million by weight). (Calculated 5500 ppm).

EXAMPLE 2

To a flask containing 343 parts of the solution containing the carboxylic acid functional quaternary ammonium compound prepared in accordance with Example 1(a) is added 84 parts of aminopropyltriethoxysilane. An exotherm of 20° C. is observed. The reactants are then mixed for 2 hours without further heating. After removing the solvent in vacuum at 60° C., a brown taffy-like liquid is obtained. Infrared Analysis indicates that the product is a quaternary ammonium compound. The chloride content of the resultant product is found to be about 3.2 percent. (Calculated 3.1 percent). The product cures to a glass-like film when exposed to atmospheric moisture.

EXAMPLE 3

(a) Preparation of 2-aminoethyl-3-aminopropyl functional polydimethylsiloxane.

A flask containing 222 parts of 2-aminoethyl-3-aminopropyltrimethoxysilane, 1110 parts of octamethylcyclotetrasiloxane and 1.5 parts potassium hydroxide is heated for 3 hours at 145° C. and then cooled to 100° C. About 1.5 parts of glacial acetic acid are added to the reaction mixture and then filtered. A clear liquid having a base equivalent of 1.5 milliequivalents/g is obtained.

(b) The procedure of Example 1(c) is repeated except that 113.8 parts of the 2-aminoethyl-3-aminopropyl functional polydimethylsiloxane prepared in 3(a) above is substituted for the 3-aminopropyl functional polydimethylsiloxane prepared in Example 1(b) above.

A transparent amber liquid is obtained which forms a gum-like polymer when the solvent is removed in the presence of atmospheric moisture. The product is identified as being a quaternary ammonium functional polydimethylsiloxane by Infrared Analysis.

EXAMPLE 4

(a) Preparation of aminofunctional polydimethylsiloxane.

A flask containing 1802.8 parts of octamethylcyclotetrasiloxane, 850 parts of eicosamethylnonasiloxane, and 2.5 parts of potassium hydroxide is heated to 150° C. About 278 parts of 2-aminoethyl-3-aminopropyltrimethoxysilane are mixed with 278 parts of water, and then slowly added to the flask, which is maintained at 150° C. for a period of 3 hours. After the addition is complete the reaction mixture is cooled to 100° C. and then 2.5 parts of glacial acetic acid are added. The resultant product is cooled to room temperature and filtered. A clear, liquid having a viscosity of 71.9 cs at 25° C. and a base equivalent of 0.75 milliequivalents/g is recovered.

(b) Preparation of quaternary ammonium functional polydimethylsiloxane.

The procedure of Example 1(c) is repeated except that 224 parts of 2-aminoethyl-3-aminopropyl functional polydimethylsiloxane prepared in 4(a) above is substituted for the 3-aminopropyl functional dimethylpolysiloxane prepared in Example 1(b) above.

The resultant product is vacuum stripped for 3 hours at 85° C. An opaque, amber liquid is recovered having a viscosity of 200,000 cs. at 25° C. It is identified by Infrared Analysis as being a quaternary ammonium functional polydimethylsiloxane.

EXAMPLE 5

(a) Preparation of 2-aminoethyl-3-aminopropyl functional polydimethylsiloxane.

A 2-aminoethyl-3-aminopropyl functional polydimethylsiloxane is prepared by reacting 2-aminoethyl-3-aminopropyltrimethoxysilane with a dimethylpolysiloxane diol. The resultant polydimethylsiloxane has the formula

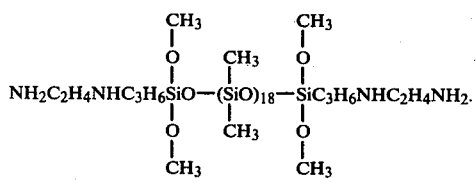

(b) Preparation of quaternary ammonium functional organopolysiloxane.

The procedure of Example 1(c) is repeated except that 72.6 parts of the 2-aminoethyl-3-aminopropyl functional polydimethylsiloxane prepared in 5(a) above is substituted for the ethoxy endblocked 3-aminopropyl functional dimethylpolysiloxane prepared in Example 1(b).

The quaternary ammonium functional polydimethylsiloxane thus formed is vacuum stripped for 3 hours at 85° C.

The resultant product is an amber, gum-like polymer which upon exposure to the atmospheric moisture formed a rubber-like film.

EXAMPLE 6

(a) Preparation of carboxylic acid functional quaternary ammonium compound.

The procedure of Example 1(a) is repeated except that 234.7 parts of phthalic anhydride are reacted with the carbinol functional quaternary compound. The acid content of the solution is about 1.0 milliequivalents. (Calculated 1.07 milliequivalents/g).

(b) Preparation of a quaternary ammonium functional polydimethylsiloxane.

A flask containing about 168 parts of the solution containing the carboxylic acid functional quaternary ammonium compound prepared in Example 6(a) above and 400 parts of the 3-aminopropyl functional polydimethylsiloxane prepared in accordance with Example 1(b) is heated for 3 hours at 65° C. and then filtered. The resultant filtrate has a chloride content of about 5,000 ppm. (Calculated 5,620 ppm). It has a nitrogen content of about 6000 ppm. (Calculated 6,373 ppm).

EXAMPLE 7

(a) Preparation of a carboxylic acid functional quaternary ammonium compound.

A flask containing 320 parts of a carbinol functional quaternary ammonium compound represented by the formula

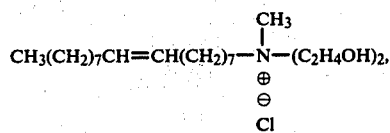

187.3 parts of succinic acid and 925 parts of toluene are refluxed until about 27 parts of water are azeotroped off. The reaction mixture is cooled to room temperature. The acid content of the mixture is 1.17 milliequivalents/g. (Calculated 1.1 milliequivalents/g). The chloride content is 1.8 percent. (Calculated chloride content is 2.0 percent).

(b) Preparation of a quaternary ammonium functional silicon compound.

To a flask containing about 343 parts of the solution containing the carboxylic acid functional quaternary ammonium compound prepared in Example 7(a) above is added 45 parts of 2-aminoethyl-3-aminopropyltrimethoxysilane. The temperature of the reaction mixture increased to about 40° C. due to the exotherm. After stirring for 2 hours without heating, the solvent is then removed in vacuum at 60° C. A brown taffy-like liquid is obtained which upon exposure to atmospheric moisture cures to a glass-like film.

EXAMPLE 8

(a) Preparation of a carboxylic acid functional quaternary ammonium compound.

To a flask containing 320 parts of a carbinol functional quaternary ammonium compound having the formula

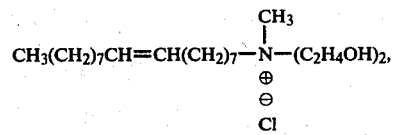

365.2 parts of 1,12 dodecanedioic acid and 925 parts of xylene are refluxed until about 27 parts of water are azeotroped off. The reaction mixture is then cooled to room temperature. The acid content of the resultant solution is 0.9 milliequivalents/g. (Calculated 0.96 milliequivalents/g). The chloride content is 1.60 percent, (calculated 1.8 percent) and the nitrogen content of the resultant product is 0.6 percent, (calculated 0.7 percent).

(b) Preparation of quaternary ammonium functional silicon compound.

To a flask containing about 350 parts of the solution containing the carboxylic acid functional quaternary ammonium compound prepared in Example 8(a) above is added 35 parts of 2-aminoethyl-3-aminopropyl trimethoxysilane. An exotherm of about 12° C. is observed. The reaction mixture is mixed for 2 hours at a temperature of about 36° C. The solvent is then removed in vacuum at 100° C. A brown, taffy-like liquid is obtained which upon exposure to atmospheric moisture, cures to a glass-like film. The chloride content of the resultant product is about 1.4 percent. (Calculated chloride content is 1.6 percent).

EXAMPLE 9

The procedure of Example 1 is repeated except that glutaconic anhydride is substituted for the succinic anhydride. A quaternary ammonium functional polydimethylsiloxane is obtained.

EXAMPLE 10

The procedure of Example 1 is repeated except that 1,2-cyclohexane dicarboxylic anhydride is substituted for the succinic anhydride. A quaternary ammonium functional polydimethylsiloxane is obtained.

EXAMPLE 11

(a) Preparation of a carboxylic acid functional quaternary ammonium compound.

To a flask containing about 129.8 parts of a carbinol functional ammonium compound having the formula

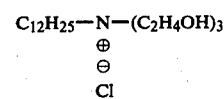

is added about 110.3 parts of succinic anhydride and heated at 100° C. for 10 hours. The resultant quaternary ammonium compound has a chloride content of 5.1 percent. (Calculated 5.7 percent). It has a nitrogen content of 2.0 percent, (calculated 2.2 percent), and an acid content of 5.0 milliequivalents/g, (calculated 4.6 milliequivalents/g).

(b) Preparation of quaternary ammonium functional polydimethylsiloxane.

To a flask containing 65.4 parts of the product prepared in Example 11(a) are added 500 parts of a trimethylsiloxy end-blocked 3-aminopropyl functional polydimethylsiloxane having a base content of 0.2 milliequivalents/g.

The resultant product is an amber gum and has an acid content of 0.4 milliequivalents/g, (calculated 0.36 milliequivalents/g) and a chloride content of 5,550 ppm, (calculated 6,600 ppm).

EXAMPLE 12

To illustrate the antistatic properties of the quaternary ammonium functional silicon compounds of this invention, a 5 percent by weight solution in 1-propanol of the compounds prepared in the Examples are padded onto 100 percent polyester fabric at a 70 percent wet pick-up rate. The treated fabric is dried for 60 seconds at 175° C. The surface resistivity, of the treated fabric is shown in the following table.

| Composition Example No. | Fabric | Surface Resistivity Ohms |
|---|---|---|
| 2 | Dacron T-54 | $1.5 \times 10^{10}$ |
| 4 | Dacron T-54 | $2.9 \times 10^{12}$ |
| None | Dacron T-54 | $1.02 \times 10^{15}$ |

What is claimed is:

1. A process for preparing quaternary ammonium functional silicon compounds which comprises reacting a carboxylic acid functional quaternary ammonium compound selected from the group consisting of compounds having the formulas

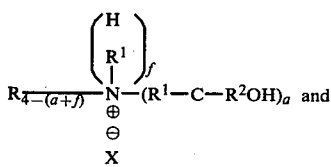 and

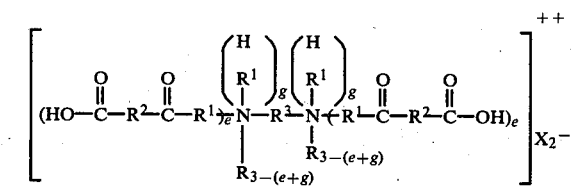

with an aminofunctional silicon compound selected from the group consisting of
(a) Silanes having the formula

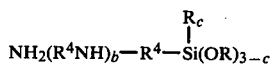

(b) Siloxanes having at least one unit of the formula

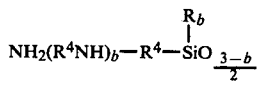

(c) and mixtures thereof, at a temperature of from 0° up to about 175° C., in which R is a monovalent hydrocarbon radical having from 1 to 22 carbon atoms, $R^1$ is a hydrocarbonoxy radical having the formula $-(C_nH_{2n}O)_r$, $R^2$ is a divalent hydrocarbon radical selected from the group consisting of $(CH_2)_y$, $CH=CH$ and cyclic divalent hydrocarbon radicals selected from the group consisting of $C_6H_4$, $C_6H_8$, $C_6H_{10}$, and $C_{10}H_6$, $R^3$ is a divalent hydrocarbon radical having from 2 to 10 carbon atoms, $R^4$ is selected from the group consisting of a saturated divalent hydrocarbon radical having up to 10 carbon atoms, a divalent hydrocarbonoxy radical in which the oxygen is in the form of an ether linkage and an unsaturated divalent hydrocarbon radical having from 3 to 10 carbon atoms, X is an anionic radical, a is a number of from 1 to 4, b is 0, 1 or 2, c is 0, 1, 2 or 3, e is a number of from 1 to 3, f is a number of from 0 to 3, in which the sum of $a+f$ cannot exceed 4, g is a number of from 0 to 2, in which the sum of $e+g$ cannot exceed 3, n is 2, 3 or 4, r is a number of from 1 to 50 and y is a number of from 0 to 10.

2. The process of claim 1, wherein the reaction is conducted in the presence of a non-protic solvent.

3. The process of claim 1, wherein the aminofunctional silicon compound is a silane having the formula

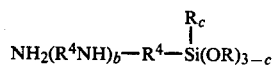

where R is a monovalent hydrocarbon radical having from 1 to 22 carbon atoms, $R^4$ is selected from the group consisting of a saturated divalent hydrocarbon radical having up to 10 carbon atoms, a divalent hydrocarbonoxy radical in which the oxygen is in the form of an ether linkage and an unsaturated divalent hydrocarbon radical having from 3 to 10 carbon atoms, b is 0, 1 or 2, and c is 0, 1, 2 or 3.

4. The process of claim 1, wherein the aminofunctional silicon compound is a siloxane having at least one unit of the formula

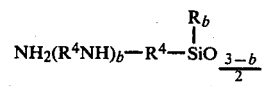

where R is a monovalent hydrocarbon radical having from 1 to 22 carbon atoms, $R^4$ is selected from the group consisting of a saturated divalent hydrocarbon radical having up to 10 carbon atoms, a divalent hydrocarbonoxy radical in which the oxygen is in the form of an ether linkage and an unsaturated divalent hydrocarbon radical having from 3 to 10 carbon atoms, and b is 0, 1 or 2.

5. The process of claim 1, wherein the aminofunctional silicon compound is a siloxane having units of the formulas

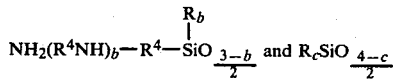

where R is a monovalent hydrocarbon radical having from 1 to 22 carbon atoms, $R^4$ is selected from the group consisting of a saturated divalent hydrocarbon radical having up to 10 carbon atoms, a divalent hydrocarbonoxy radical in which the oxygen is in the form of an ether linkage and an unsaturated divalent hydrocarbon radical having from 3 to 10 carbon atoms, b is 0, 1 or 2 and c is 0, 1, 2 or 3.

6. The process of claim 1, wherein the mole ratio of the carboxylic acid groups of the carboxylic acid quaternary ammonium compound to amine groups of the aminofunctional silicon compound is in the range of from 4:1 to 1:3 with the proviso that at least one carboxylic acid group is reacted with one amine group.

7. The process of claim 1, wherein the carboxylic acid functional quaternary ammonium compound is represented by the formula

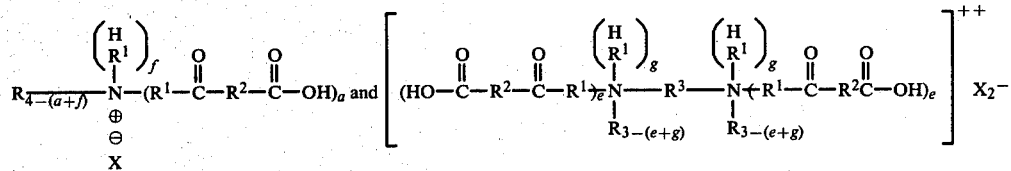

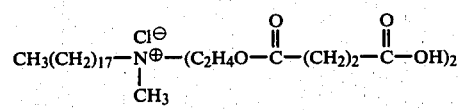

8. The process of claim 1, wherein the carboxylic acid functional quaternary ammonium compound is represented by the formula

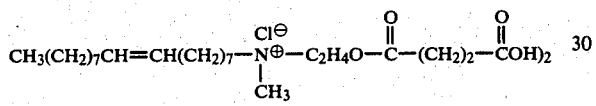

9. The process of claim 1, wherein the aminofunctional siloxanes have at least one unit of the formula

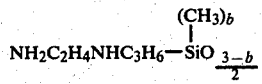

where b is 0, 1 or 2.

10. The process of claim 1, wherein the aminofunctional siloxanes have at least one unit of the formula

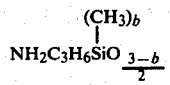

where b is 0, 1 or 2.

11. The process of claim 1, wherein the aminofunctional siloxanes have at least one unit of the formula

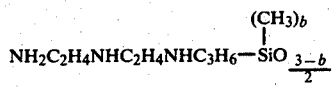

where b is 0, 1 or 2.

12. The composition prepared in accordance with the process of claim 1.

13. The composition prepared in accordance with the process of claim 3.

14. The composition prepared in accordance with the process of claim 4.

15. A process for imparting antistatic properties to textile materials which comprises applying to the textile materials a composition obtained from the reaction of a carboxylic acid functional quaternary ammonium compound selected from the group consisting of compounds having the formulas

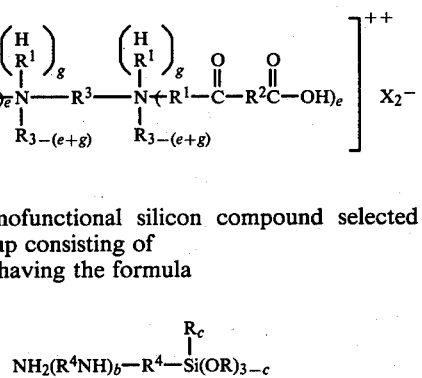

with an aminofunctional silicon compound selected from the group consisting of (a) Silanes having the formula $$NH_2(R^4NH)_b-R^4-Si(OR)_{3-c}^{R_c}$$

(b) Siloxanes having at least one unit of the formula $$NH_2(R^4NH)_b-R^4-SiO_{\frac{3-b}{2}}^{R_b}$$

(c) and mixtures thereof,
at a temperature of from 0° up to about 175° C., in which R is a monovalent hydrocarbon radical having from 1 to 22 carbon atoms, $R^1$ is a hydrocarbonoxy radical having the formula $-(C_nH_{2n}O)_2$, $R^2$ is a divalent hydrocarbon radical selected from the group consisting of $(CH_2)_y$, $CH=CH$ and a cyclic divalent hydrocarbon radical selected from the group consisting of $C_6H_4$, $C_6H_8$, $C_6H_{10}$, and $C_{10}H_6$, $R^3$ is a divalent hydrocarbon radical having from 2 to 10 carbon atoms, $R^4$ is selected from the group consisting of a saturated divalent hydrocarbon radical having up to 10 carbon atoms, a divalent hydrocarbonoxy radical in which the oxygen is in the form of an ether linkage and an unsaturated divalent hydrocarbon radical having from 3 to 10 carbon atoms, X is an anionic radical, a is a number of from 1 to 4, b is 0, 1 or 2, c is 0, 1, 2 or 3, e is a number of from 1 to 3, f is a number of from 0 to 3, in which the sum of a+f cannot exceed 4, g is a number of from 0 to 2, in which the sum of e+g cannot exceed 3, n is 2, 3 or 4, r is a number of from 1 to 50 and y is a number of from 0 to 10 and thereafter heating the treated textile material at an elevated temperature.

16. The process of claim 15, wherein the composition contains a non-protic solvent.

17. The process of claim 15, wherein the composition is dispersed in water.

18. The process of claim 15, wherein the treated textile material is heated to a temperature up to about 200° C.

* * * * *

UNITED STATES PATENT AND TRADEMARK OFFICE
CERTIFICATE OF CORRECTION

PATENT NO. : 4,394,517
DATED : July 19, 1983
INVENTOR(S) : Eugene R. Martin and Jeffrey A. Tripp It is certified that error appears in the above-identified patent and that said Letters Patent are hereby corrected as shown below:

Claim 1, lines 30 to 35, which reads,

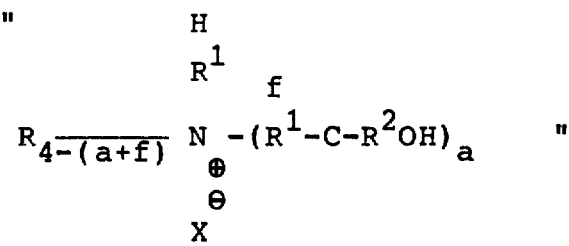

should read

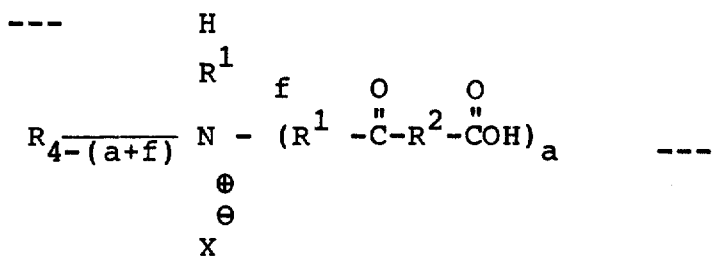

Signed and Sealed this

Thirteenth Day of March 1984

[SEAL]

Attest:

GERALD J. MOSSINGHOFF

Attesting Officer  Commissioner of Patents and Trademarks